United States Patent [19]

Schmalstieg et al.

[11] Patent Number: 5,096,994

[45] Date of Patent: Mar. 17, 1992

[54] POLYISOCYANATES CONTAINING ESTER GROUPS, A PROCESS FOR THE PRODUCTION OF THESE POLYISOCYANATES AND THEIR USE IN POLYURETHANE COATING COMPOSITIONS

[75] Inventors: Lutz Schmalstieg; Josef Pedain, Cologne; Klaus Nachtkamp, Duesseldorf; Lothar Kahl, Bergisch Gladbach; Manfred Schönfelder, Leverkusen, all of Fed. Rep. of Germany

[73] Assignee: Bayer Aktiengesellschaft, Leverkusen Bayerwerk, Fed. Rep. of Germany

[21] Appl. No.: 561,770

[22] Filed: Aug. 2, 1990

[30] Foreign Application Priority Data

Aug. 10, 1989 [DE] Fed. Rep. of Germany ....... 3926389

[51] Int. Cl.$^5$ .......................... C07C 69/76; C07F 7/10
[52] U.S. Cl. ........................ 128/69; 560/106; 560/129; 560/130; 560/344; 560/336; 556/414
[58] Field of Search .................. 528/69; 560/130, 129, 560/344, 336, 106; 556/414

[56] References Cited

U.S. PATENT DOCUMENTS

| | | | |
|---|---|---|---|
| 3,870,556 | 3/1975 | Noll et al. | 117/141 |
| 3,903,127 | 9/1975 | Wagner et al. | 260/453 |
| 3,912,770 | 10/1975 | Botta et al. | 260/404 |
| 4,614,785 | 9/1986 | Richter et al. | 528/45 |
| 4,745,212 | 5/1988 | Mormann et al. | 560/130 |
| 4,801,663 | 1/1989 | Ueyanagi et al. | 525/528 |
| 4,870,198 | 9/1989 | Mormann et al. | 556/414 |
| 4,886,902 | 12/1989 | Mormann et al. | 560/106 |
| 4,946,990 | 8/1990 | Mormann et al. | 560/106 |

Primary Examiner—John Kight, III
Assistant Examiner—Duc Truong
Attorney, Agent, or Firm—Joseph C. Gil

[57] ABSTRACT

The present invention relates to polyisocyanates which contain ester groups and have
a) a content of aliphatically bound isocyanate groups of 18 to 33% by weight,
b) an average NCO functionality of 4.1 to 10, preferably from 4.5 to 10, and
c) a viscosity of 200 to 2,5000 mPa.s at 22° C.

The present invention also relates to preferred polyisocyanates which contain ester groups and have
a) a content of aliphatically bound isocyanate groups of 20 to 33% by weight,
b) an average NCO functionality of 5 to 8 and
c) a viscosity of 500 to 1,000 mPa.s at 22° C.

The present invention further relates to a process for the preparation of these preferred polyisocyanates by reacting isocyanatocarboxylic acid chlorides with O-silylated, polyhydric alcohols at a temperature of about 50° to 150° C. Finally, the present invention relates to the use of the polyisocyanates as the isocyanate component for two-component polyurethane coating compositions.

4 Claims, No Drawings

POLYISOCYANATES CONTAINING ESTER GROUPS, A PROCESS FOR THE PRODUCTION OF THESE POLYISOCYANATES AND THEIR USE IN POLYURETHANE COATING COMPOSITIONS

BACKGROUND OF THE INVENTION

1. Field of the Invention

This invention relates to aliphatic polyisocyanates containing ester groups which combine particularly high functionality with extremely low viscosity, to a process for the production of these polyisocyanates and to their use as the isocyanate component in two-component polyurethane coating compositions.

2. Description of the Prior Art

Relatively high functionality polyisocyanates containing aliphatically bound isocyanate groups have acquired considerable economic and industrial significance as the isocyanate component for two-component polyurethane coating compositions. Known polyisocyanates for use in polyurethane coating compositions are generally produced by biuretization, trimerization or urethanization of low molecular weight diisocyanates, particularly hexamethylene diisocyanate.

There are several known processes for the production of aliphatic biuret polyisocyanates. Monomer-free, commercially available polyisocyanates produced by biuretization generally have average functionalities of 3 to 4. The products having a high functionality, i.e., products having a functionality of about 4, inevitably have a higher viscosity than those of low functionality, i.e. products having a functionality of about 3.

Biuret polyisocyanates having a particularly low viscosity are described, for example, in US-PS 3,903,127. The interdependence of functionality and viscosity is impressively demonstrated by Example 3 of this patent. The polyisocyanate having a functionality of 3 has a viscosity of 750 mPa.s/20° C. (Example 3e). If the mixture contains 18% products of higher functionality, its viscosity rises to 1,350 mPa.s/20° C. (Example 3b). If the percentage of products of higher functionality increases to 28%, the mixture has a viscosity of 2,560 mPa.s/20° C. (Example 3a).

The production of isocyanurate polyisocyanates is also described in numerous publications, the conditions are similar. Again, the products with higher functionalities also have higher viscosities. However, the isocyanurate polyisocyanates having an average functionality of 3 to 4 have a somewhat lower viscosity than the biuret polyisocyanates having a comparable functionality. DE-OS 3 810 908, for example, describes isocyanurate polyisocyanates of particularly low viscosity. If the oligomer mixture contains 30% of the products having a functionality of greater than 3, its viscosity is 1,300 mPa.s/25° C. (Example I). If the mixture contains 25% of products having a functionality of greater than 3, its viscosity is only 1,000 mPa.s/25° C. (Example 2).

The production of polyisocyanates for polyurethane coating compositions by urethanization of low molecular weight diisocyanates with polyhydric alcohols results in high viscosity to resin-like products which can only be processed by the addition of organic solvents.

Considerably lower viscosities are only shown by polyisocyanates containing a high percentage of uretdione structures also possess considerably lower viscosities, as described for example in U.S. Pat. No. 4,614,785. However, these polyisocyanates generally have an average functionality below 3, which means that the low viscosity is accompanied by the disadvantage of a low functionality.

The average NCO functionality is of considerable importance in regard to the suitability of the polyisocyanates for the production of high-quality coatings. The higher the functionality, the higher the crosslink density in the coating and, thus, the higher its resistance. However, the higher viscosities associated with the high functionalities are a disadvantage because they necessitate the increased use of organic solvents for establishing the necessary application viscosities.

Accordingly, it is an object of the present invention to provide new polyisocyanates which combine high functionality with low viscosity, so that they may be used for the production of high-quality, low-solvent or solventless two-component polyurethane coating compositions.

This object was achieved in accordance with the present invention by the polyisocyanates described in detail hereinafter. The new polyisocyanates according to the invention have a viscosity of at most 2,500 mPa.s/22° C., preferably at most 1,000 mPa.s/22° C., and an average functionality of at least 4.1, preferably at least 4.5 and more preferably at least 5.

In terms of chemical structure, the new polyisocyanates contain ester groups, have an average molecular weight below 2,000 and an average functionality of at least 4.1.

Polyisocyanates containing ester groups are known. DE-OS 2 120 090 describes polyisocyanate prepolymers which contain ester groups, have an average molecular weight of about 900 to 20,000 and are suitable for the finishing of textiles. These products are applied from dilute solutions. They are not suitable for the formulation of low-solvent two-component coating compositions. DE-OS 3 634 248 describes a process for the production of polyisocyanates which contain ester groups. However, the polyisocyanates described in DE-OS 3 634 248 do not have the high functionality required by the polyisocyanates of the present invention because the polyisocyanates containing ester groups are produced solely by reaction of alcohols having a maximum functionality of 4 to form polyisocyanates which have a functionality which corresponds to the functionality of the polyhydric alcohols from which they are prepared. This reference does not disclose polyisocyanate mixtures based on tetrahydric alcohols which, in addition to the corresponding tetrafunctional polyisocyanates, also contain homologs of higher functionality such that the average functionality is at least 4.1, nor does the reference disclose a process for the production of high functionality, low viscosity polyisocyanates containing ester groups based on polyols having a functionality of 5 or higher.

SUMMARY OF THE INVENTION

The present invention relates to polyisocyanates which contain ester groups and have
a) a content of aliphatically bound isocyanate groups of 18 to 33% by weight,
b) an average NCO functionality of 4.1 to 10, preferably from 4.5 to 10, and
c) a viscosity of 200 to 2,500 mPa.s at 22° C.

The present invention also relates to preferred polyisocyanates which contain ester groups and have
a) a content of aliphatically bound isocyanate groups of 20 to 33% by weight, b) an average NCO functionality of 5 to 8 and
c) a viscosity of 500 to 1,000 mPa.s at 22° C.

The present invention further relates to a process for the preparation of these preferred polyisocyanates by reacting isocyanatocarboxylic acid chlorides corresponding to the formula OCN—R—COCl wherein
R is a saturated, aliphatic hydrocarbon radical containing 2 to 5 carbon atoms,
with O-silylated, polyhydric alcohols at a temperature of about 50° to 150° C. with removal of the trisubstituted chlorosilane formed by distillation, characterized in that sugars or sugar alcohols containing 5 and/or 6 hydroxyl groups, in which all the hydroxyl groups are present in silylated form, are used as the O-silylated polyhydric alcohols.

Finally, the present invention relates to the use of the polyisocyanates as the isocyanate component for two-component polyurethane coating compositions.

DETAILED DESCRIPTION OF THE INVENTION

The preferred polyisocyanates according to the invention have an average NCO functionality of at least 4.5.

The particularly preferred polyisocyanates or polyisocyanate mixtures according to the invention are based on pentahydric and/or hexahydric alcohols and are produced by the process according to the invention.

The polyisocyanates according to the invention are prepared by reacting isocyanatocarboxylic acid chlorides with O-silylated polyhydric alcohols. Sugars and/or sugar alcohols containing five and/or six hydroxyl groups per molecule, in which all of the hydroxyl groups are present in silylated form, are used for the production of the particularly preferred polyisocyanates according to the invention.

Suitable isocyanatocarboxylic acid chlorides are, in particular, compounds corresponding to the formula OCN—R—COCl wherein
R is a difunctional, saturated, aliphatic hydrocarbon radical containing 2 to 5 carbon atoms, at least 2 carbon atoms being arranged between the isocyanate group and the chlorocarbonyl group.

3-Isocyanatopropionic acid chloride, 4-isocyanatobutyric acid chloride or 6-isocyanatocaproic acid chloride are examples of suitable isocyanatocarboxylic acid chlorides.

In the context of the invention, O-silylated hydroxyl groups are understood to be structural units corresponding to the formula R'$_3$Si—O— wherein
R' is an alkyl or aryl group, preferably a $C_{1-4}$ alkyl group and more preferably a methyl group.

Suitable reactants for the isocyanatocarboxylic acid chlorides to produce the polyisocyanates according to the invention include alcohols having 4 to 8, preferably 5 or 6 hydroxyl groups wherein the hydroxyl groups are present in silylated form. Suitable polyhydric alcohols for the production of these intermediates include pentaerythritol, mannitol, sorbitol, formitol, fructose, glucose, sucrose, lactose and any other sugars or sugar alcohols containing 4 to 8 hydroxyl groups per molecule. Mixtures of these polyhydric alcohols may also be used.

The silylated starting materials may be produced from these polyhydric alcohols by the methods described in M. Lalonde and C. H. Chan, Synthesis 1985, pages 817-845. The polyhydroxyl compounds may be silylated with chlorosilanes and/or disilazanes corresponding to the formula $$R'_3SiCl \text{ or } R'_3Si-\overset{H}{N}-SiR'_3$$

wherein
R' is as defined above.

The nature of the substituent R' is of secondary importance as far as the production of the polyisocyanates according to the invention is concerned.

The silylation of sugar alcohols is described by M. M. Sprung and L. S. Nelson in J. Org. Chem. 20, page 1750 (1955), while the silylation of sugars was described by F. A. Henglein and K. Scheinost in Makromol. Chem. 21, page 59 (1956).

In the production of the polyisocyanates, the quantities of isocyanatocarboxylic acid chloride and silyl ether are preferably selected such that there are 1.0 to 1.2 moles of silylated hydroxyl groups for every mole of chlorocarbonyl groups. It is most preferred to use equimolar quantities of the starting materials. The reaction of the silylated hydroxyl compounds with isocyanatocarboxylic acid chlorides is carried out at a temperature of about 50° to 150° C., preferably about 60° to 100° C.

The reaction may optionally be carried out in the presence of catalysts which are known for this reaction such as pyridine or quinoline. The reaction may also be carried out in the presence of inert solvents, although it is preferred not to use solvents. The trisubstituted chlorosilane, preferably trimethyl chlorosilane, formed during the reaction from the silylated hydroxyl groups as a secondary product may be removed from the reaction mixture by distillation and is preferably distilled off continuously during the reaction.

In the preferred process where an excess of chlorocarbonyl groups over silylated hydroxyl groups is avoided, substantially chlorine-free polyisocyanate mixtures containing ester groups are formed during the reaction. The polyisocyanates possess the properties mentioned above and may be used in accordance with the invention without further working up by distillation. As shown by gel chromatographic analysis the polyisocyanates are generally mixtures of polyisocyanates having a functionality corresponding to the alcohol used as the principal component and polyisocyanates having twice and three times the molecular weight of this alcohol as secondary components. Accordingly, the average functionality calculated from the isocyanate content and from the molecular weight as determined by vapor pressure osmometry is always at least 4.1, preferably at least 4.5, even when tetrahydric alcohols are exclusively used as the alcohol component.

When pentahydric and higher functional alcohols are used, the procedure described above is preferably used. This means that care is preferably taken to use at most equivalent quantities of carboxylic acid chloride and silylated hydroxyl groups in the reaction so that substantially chlorine-free polyisocyanates are formed as the reaction products. The polyisocyanates have an average functionality which is higher than the functionality of the alcohol used and may be used in accordance with the invention in undistilled form. However, it is also possible on completion of the process to work up the reaction products obtained, for example, by high vacuum distillation, so that the principal component (having a functionality which corresponds to the functionality of the alcohol used) accumulates as distillate. When the reaction mixtures are worked up by distillation, it is possible to use larger than equimolar quantities of isocyanatocarboxylic acid chloride, i.e., up to 1.2 times the equivalent quantity, based on the silylated alcohols. Although larger excesses are possible, they generally only lead to losses of yield without any corresponding improvement.

In accordance with these observations, the particularly preferred polyisocyanates are formed in the process according to the invention from penta- and/or hexahydric alcohols in O-silylated form and have an (average) NCO functionality of 5 to 8.

The polyisocyanates according to the invention are distinguished by the absence of monomers and by extremely low viscosities. By using mixtures of different silylated polyalcohols, it is possible to produce polyisocyanates having any desired functionality. By virtue of their properties, the polyisocyanates according to the invention are eminently suitable for the production of low-solvent or solventless two-component polyurethane coating compositions.

The preferred reactants to be used in combination with the polyisocyanates according to the invention for the production of polyurethane coating compositions are the polyhydroxy polyesters, polyethers and polyacrylates and, optionally, low molecular weight polyhydric alcohols known per se from polyurethane coating composition technology. Polyamines, particularly in blocked form as polyketimines or oxazolidines, may also be used as reactants for the products according to the invention. These reactants contain an average of at least two isocyanate-reactive groups. The quantitative ratios in which the polyisocyanates and the isocyanate-reactive components are used for the production of the polyurethane coating compositions are selected such that there are 0.8 to 3, preferably 0.9 to 1.1, isocyanate-reactive groups for every isocyanate group.

To accelerate the cure rate of the coating compositions, it is possible to the catalysts typically used in isocyanate chemistry, for example, tertiary amines such as triethylamine, pyridine, methyl pyridine, benzyl dimethylamine, N,N-dimethylaminocyclohexane, N-methyl piperidine, pentamethyl diethylenetriamine, N,N'-endoethylene piperazine and N,N'-dimethyl piperazine; and metal salts such as iron(III) chloride, zinc chloride, zinc-2-ethyl caproate, tin(II)-2-ethyl caproate, dibutyltin(IV) dilaurate and molybdenum glycolate.

The coating compositions containing the polyisocyanates according to the invention may be used to produce films which adhere surprisingly firmly to metallic substrates and are particularly light-stable, heat-stable and abrasion-resistant. They are also distinguished by high elasticity, high hardness, very good resistance to chemicals, high gloss, excellent weathering resistance and good pigmentability.

In addition to the reactive components, the coating compositions may optionally contain the pigments, flow control agents, fillers, etc., which are known from coatings technology.

The invention is illustrated by the following examples. A comparison of the properties of a two-component polyurethane coating composition according to the invention with those of a polyurethane coating composition which does not correspond to the invention illustrates, in particular, the increase in solids content for the same viscosity which is made possible by the invention. All parts and percentages are by weight unless otherwise indicated.

EXAMPLES

Example 1

Preparation of a Polyisocyanate Mixture 424 g (1 mole) 2,2-bis-trimethylsiloxymethyl-1,3-bis-trimethylsiloxypropane, prepared by the silylation of pentaerythritol in accordance with K. M. Sprung, L. S. Nelson, J. Org. Chem. 20, page 1750 (1955), and 702 g (4 moles) 6-isocyanatocaproic acid chloride were stirred at 90° to 100° C. with the addition of 1 ml pyridine until the IR spectrum no longer showed the acid chloride band. The trimethyl chlorosilane formed was continuously distilled off during the reaction. After final traces of trimethyl chlorosilane were removed by thin-layer distillation, a polyisocyanate having the following characteristic data was obtained:

NCO content: 22.6%.

Viscosity at 22° C.: 210 mPa.s.

The molecular weigh ($M_w$), as determined by vapor pressure osmometry, was 880, from which a functionality of 4.73 was calculated.

The gel chromatogram showed 77% surface area of a product having a theoretical molecular weight of 692 g, 15.3% of a product having twice this molecular weight and 7.7% of a product having three times this molecular weight.

Example 2

Preparation of a Polyisocyanate Mixture 614 g (1 mole) hexatrimethylsiloxymannitol prepared by the silylation of mannitol in accordance with K. M. Sprung, L. S. Nelson, J. Org. Chem. 20, page 1750 (1955) and 1053.6 g (6 moles) 6-isocyanatocaproic acid chloride were reacted as described in Example 1. After the final traces of trimethyl chlorosilane were removed by thin-layer distillation, a product having the following characteristic data was obtained:

NCO content: 23.1%.

Viscosity at 22° C.: 750 mPa.s.

The average molecular weight ($M_w$) as determined by vapor pressure osmometry was 1110, from which a functionality of 6.56 was calculated.

Analysis of the product mixture by gel chromatography showed 81% surface area of a product having a theoretical molecular weight of 1016, 16% of a product having twice this molecular weight and 3% of product having three times this molecular weight.

Example 3

Preparation of a Polyisocyanate Mixture 540 g (1 mole) pentatrimethylsiloxyglucose prepared in accordance with F. A. Henglein, K. Scheinost, Makromol. Chem. 21, page 59 (1956) and 877.5 g (5 moles) 6-isocyanatocaproic acid chloride were reacted as described in Example 1. After the final traces of trimethyl chlorosilane were removed by thin-layer distillation, a product having the following characteristic data was obtained:
NCO content: 22.4%.
Viscosity at 22° C.: 800 mPa.s.

Example 4

Preparation of a Polyisocyanate Mixture 614 g (1 mole) hexatrimethylsiloxysorbitol prepared by the silylation of sorbitol in accordance with K. M. Sprung, L. S. Nelson, J. Org. Chem. 20, page 1750 (1955) and 801 g (6 moles) 3-isocyanatopropionic acid chloride were reacted as described in Example 1. After the removal of the final traces of trimethyl chlorosilane by thin-layer distillation, a product having the following characteristic data was obtained:
NCO content: 30.1%.
Viscosity at 22° C.: 890 mPa.s.

Example 5

Production of a Two-Component Polyurethane Coating Composition 100 parts by weight of a polyol solution containing 42 parts by weight polyacrylate polyol A, 28 parts by weight polyester polyol B and 30 parts by weight xylene were mixed with 40 parts by weight of the polyisocyanate mixture of Example 1 dissolved in 24 parts by weight methoxypropyl acetate (equivalent ratio of isocyanate groups to isocyanate-reactive groups =1:1).
Solids content: 67% .
Flow time: 25 sec. (DIN cup 4)
Test results of the coating composition films:
Stoving conditions: 30 mins. at 120° C.
König pendulum hardness, DIN 53 157: 185 secs.
Erichsen indentation, DIN/ISO 1520: 10.0 mm.

Polyacrylate polyol A

Copolymer containing 5.45% hydroxyl groups and 1.2% carboxyl groups and prepared by the reaction of
38.8 parts by weight hydroxypropyl methacrylate
21.6 parts by weight styrene
21.6 parts by weight methyl methacrylate
16 parts by weight butyl acrylate
2 parts by weight acrylic acid

Polyester polyol B

Polyester polyol containing 4.85% hydroxyl groups prepared by the reaction of
19.5 parts by weight 2-ethyl hexanoic acid
41.2 parts by weight trimethylol propane
28.5 parts by weight hexahydrophthalic anhydride
10.8 parts by weight adipic acid

Example 6 (Comparison)

Production of a Two-Component Polyurethane Coating Composition Based on a Polyisocyanate Mixture Containing Isocyanurate Groups 100 parts by weight of the polyol solution of Example 5 were mixed with 42 parts by weight of a hexamethylene diisocyanate-based polyisocyanurate polyisocyanate having an NCO content of 21.5% and a viscosity of 3,000 mPa.s/22° C. (average molecular weight ($M_w$) as determined by vapor pressure osmometry =760, functionality TM 3.89) dissolved in 40 parts by weight methoxypropyl acetate (equivalent ratio of isocyanate groups to isocyanate-reactive groups TM 1:1).
Solids content: 61.5% .
Flow time: 25 secs. (DIN cup 4).
Test results of the coating composition films:
Stoving conditions: 30 mins. at 120° C.
König pendulum hardness, DIN 53 157: 191 secs.
Erichsen indentation, DIN/ISO 1520: 10.2 mm Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polyisocyanate which contains ester groups and has
   a) a content of aliphatically bound isocyanate groups of 18 to 33% by weight,
   b) an average NCO functionality of 4.5 to 10 and
   c) a viscosity of 200 to 2,500 mPa.s at 22° C.

2. The polyisocyanate of claim 1 which has
   a) a content of aliphatically bound isocyanate groups of 20 to 33% by weight,
   b) an average NCO functionality of 5 to 8 and
   c) a viscosity of 500 to 1,000 mPa.s at 22° C.

3. A process for the production of a polyisocyanate which contains ester groups and has
   a) content of aliphatically bound isocyanate groups of 20 to 33% by weight,
   b) an average NCO functionality of 5 to 8 and
   c) a viscosity of 500 to 1,000 mPa.s at 22° C.,
which comprises reacting at about 50 to 150° C. an isocyanatocarboxylic acid chloride corresponding to the formula $$OCN-R-COCl$$

wherein
R is a saturated, aliphatic hydrocarbon radical containing 2 to 5 carbon atoms,
with a sugar or sugar alcohols containing 5 and/or 6 hydroxyl groups, in which all of the hydroxyl groups are present in silylated form according to the formula $$R'_3-Si-O-$$

wherein
R' is an alkyl or aryl group,
in a 1:1 equivalent ratio of chlorocarbonyl groups to silylated hydroxyl groups, and removing the trisubstituted chlorosilane formed during the reaction by distillation.

4. A two-component coating composition which comprises the polyisocyanate of claim 1 and a component containing at least two isocyanate-reactive groups.

* * * * *